US00PP26888P3

(12) United States Plant Patent
Danziger

(10) Patent No.: US PP26,888 P3
(45) Date of Patent: Jun. 28, 2016

(54) ***PETUNIA* PLANT NAMED 'DCAS303'**

(50) Latin Name: *Petunia sensu wijsman*
Varietal Denomination: DCAS303

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 118 days.

(21) Appl. No.: 14/120,182

(22) Filed: May 2, 2014

(65) Prior Publication Data

US 2015/0319904 P1 Nov. 5, 2015

(51) Int. Cl.
*A01H 5/02* (2006.01)

(52) U.S. Cl.
USPC ..... Plt./356.13

(58) Field of Classification Search
USPC ..... Plt./356.1, 356.13
See application file for complete search history.

*Primary Examiner* — Susan McCormick Ewoldt
(74) *Attorney, Agent, or Firm* — Cassandra Bright

(57) ABSTRACT

A new and distinct *Petunia* cultivar named 'DCAS303' is disclosed, characterized by abundant flowering, unique flower coloration, which changes with maturity, strong vigor and a very well branched plant with a semi-trailing form. The new variety is a *Petunia*, normally produced as an outdoor garden or container plant.

2 Drawing Sheets

Figure 1:
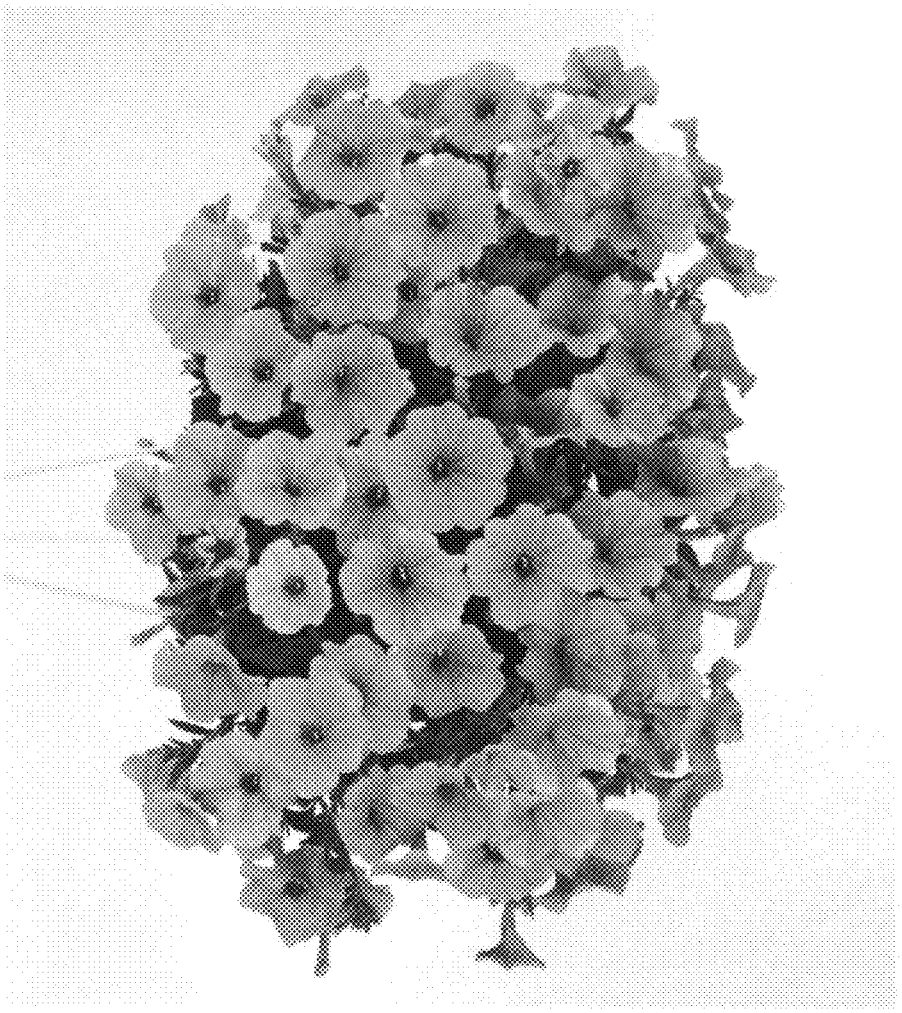

Latin name of the genus and species: *Petunia sensu wijsman.*

Variety denomination: 'DCAS303'.

BACKGROUND OF THE INVENTION

The new *Petunia* cultivar is a product of a planned breeding program conducted by the inventor, Gavriel Danziger, in Moshav Mishmar Hashiva, Israel. The objective of the breeding program was to produce new *Petunia* varieties for ornamental commercial applications. The cross resulting in this new variety was made during October of 2010.

The seed parent is the unpatented, proprietary variety referred to as *Petunia sensu wijsman*. 'cv. 7-1380'. The pollen parent is the unpatented, proprietary variety referred to as *Petunia sensu wijsman* 'cv. 10-4341', containing the black gene described in U.S. Utility Pat. No. 7,642,436. The new variety was discovered in June of 2011 by the inventor in a group of seedlings resulting from the 2010 crossing, in a research greenhouse in Moshav Mishmar Hashiva, Israel.

Asexual reproduction of the new cultivar was performed by vegetative cuttings. This was first performed at a research greenhouse in Moshav Mishmar Hashiva, Israel in July of 2011 and has shown that the unique features of this cultivar are stable and reproduced true to type in more than 25 successive generations.

SUMMARY OF THE INVENTION

The cultivar 'DCAS303' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DCAS303' These characteristics in combination distinguish 'DCAS303' as a new and distinct *Petunia* cultivar:

1. Semi-trailing growth habit.
2. Very well branched plants with strong vigor.
3. Flowers change color from yellow when opening to orange-pink, fading to pink-brown.
4. Large flower size.
5. Abundant flowering.

PARENT COMPARISON

Plants of the new cultivar 'DCAS303' are similar to plants of the seed parent, *Petunia sensu wijsman* 'cv. 7-1380' in most horticultural characteristics, however, plants of the new cultivar 'DCAS303' differ in the following:

1. Semi-trailing growth habit compared to the semi upright growth habit of the seed parent.
2. Larger plant size
3. Different flower color during various stages: yellow when opening to orange-pink, fading to pink-brown compared to pink color of the seed parent.
4. Larger flower size.
5. Greater amount of flowers.

Plants of the new cultivar 'DCAS303' are similar to plants of the pollen parent; *Petunia sensu wijsman* 'cv. 10-4341' in most horticultural characteristics, however, plants of the new cultivar 'DCAS303' differ in the following;

1. Semi-trailing growth habit compared to the trailing growth habit of pollen parent.
2. Many more branches per plant than the pollen parent.
3. Changing flower color, yellow when opening to orange-pink, fading to pink-brown compared to black with yellow striped flower color of pollen parent.
4. Smaller flower size.
5. Less abundant flowering.

COMMERCIAL COMPARISON

Plants of the new cultivar 'DCAS303' are comparable to the commercial variety *Petunia* 'DANRAY1' U.S. Plant Pat.

No. 20,974. The two *Petunia* varieties are similar in most horticultural characteristics; however, the new variety 'DCAS303' differs in the following:

1. Smaller flower size.
2. Yellow-orange-pink flowers. The comparator has white flowers.
3. Semi-trailing growth habit compared to the mounded growth habit of the comparator.

Plants of the new cultivar 'DCAS303' can also be compared to the commercial variety *Petunia* 'DANRAY3', unpatented. These varieties are similar in most horticultural characteristics; however 'DCAS303' differs in the following:

1. Smaller flower size.
2. Yellow-orange-pink flowers. The comparator has light purple flowers with dark purple veins.
3. Semi-trailing growth habit compared to the mounded growth habit of the comparator.

BRIEF DESCRIPTION OF THE PHOTOGRAPHS

The accompanying photograph in FIG. 1 illustrates in full color a typical plant of 'DCAS303' grown in a greenhouse, in a 13 cm pot. Age of the plant photographed is approximately 3 months from a rooted cutting.

Figure 2:
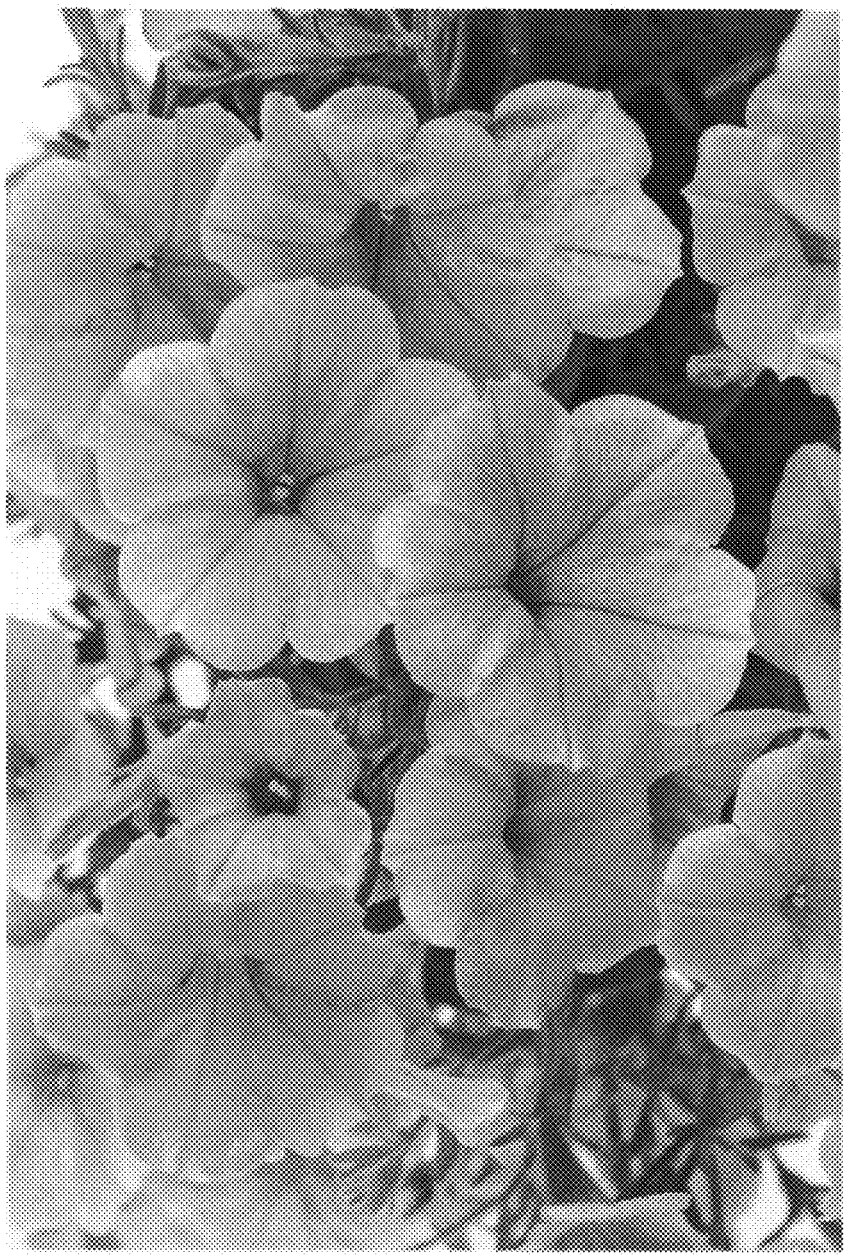

FIG. 2 illustrates in full color a close up of a typical bloom of 'DCAS303'. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2001 except where general terms of ordinary dictionary significance are used. The following observations and measurements describe 'DCAS303' plants grown in a greenhouse, in Moshav Mishmar Hashiva, Israel. The growing temperature ranged from 20° C. to 35° C. during the day and from 17° C. to 23° C. during the night. General light conditions are bright, normal sunlight. Measurements and numerical values represent averages of typical plant types.

Botanical classification: *Petunia sensu wijsman* 'DCAS303'.

PROPAGATION

Time to initiate roots: About 10 to 14 days.
Root description: Fibrous.

PLANT

Age of plant described: Approximately 60 days from a rooted cutting.
Growth habit: Mounded.
Pot size of plant described: 13 cm.
Height: About 13 cm.
Plant spread: About 60 cm.
Growth rate: Strong.
Branching characteristics: Very well branched.
Length of primary lateral branches: About 45 cm.
Diameter of lateral branches: About 0.5 cm.
Quantity of primary lateral branches: 8.
Characteristics of primary lateral branches:
- *Form*.—Cylindrical.
- *Diameter*.—About 0.5 cm.
- *Color*.—RHS Green 143 C.
- *Texture*.—Pubescent.
- *Strength*.—Good.

Internode length: About 2 cm.

FOLIAGE

Leaf:
- *Arrangement*.—Opposite.
- *Quantity*.—Approximately 30 per branch.
- *Average length*.—6.5 cm.
- *Average width*.—3.5 cm.
- *Shape of blade*.—Elliptic.
- *Apex*.—Acute.
- *Base*.—Acute.
- *Margin*.—Entire.
- *Texture of surfaces*.—Velvety.
- *Aspect*.—Mainly flat, attached at approximately 90 degrees.
- *Color*.—Young foliage upper side: RHS Green 137 B. Young foliage under side: RHS Green 137 C. Mature foliage upper side: RHS Green 137 B. Mature foliage under side: RHS Green 137 C.
- *Venation*.—Type: Pinnate. Venation color upper side: RHS Green 137 C. Venation color under side: RHS Green 137 C.
- *Petiole*.—Length: About 0.5 cm. Diameter: About 0.3 cm. Color: RHS Green 137 B.
- *Texture*.—Velvety.

FLOWER

Natural flowering season: Spring, Summer and Autumn.
Days to flowering from rooted cutting: About 30 days.
Inflorescence and flower type and habit: Axillary, single flower, Salverform shape, outwardly facing.
Rate of flower opening: 2 to 3 days from bud to fully opened flower.
Flower longevity on plant: 3-6 days.
Approximate quantity of flowers per plant: About 80.
Persistent or self-cleaning: Self-cleaning.
Bud:
- *Shape*.—Tubular.
- *Length*.—About 4.0 cm.
- *Diameter*.—About 0.8 cm.
- *Color*.—RHS Yellow-Green N144 A.

Flower size:
- *Diameter*.—About 5 cm.
- *Flower tube length*.—About 3 cm.
- *Flower tube diameter at distal end*.—1.2 cm.
- *Flower tube diameter at proximal end*.—0.4 cm.

Petals:
- *Length from throat*.—About 2 cm.
- *Width*.—About 2.5 cm.
- *Quantity*.—5.
- *Texture*.—Velvety.
- *Apex*.—Blunt.
- *Margin*.—Wavy.

Color:
- *When opening*.—Upper surface: Closest to RHS Yellow-Green 153 B, mixed with Orange-Red 34 A. Lower surface: RHS Yellow-green 151 B.
- *Fully opened*.—Upper surface: Closest to RHS Orange-Red 34 A, mixed with Yellow-Green 151 A. Lower surface: Closest to RHS Yellow-Green 151 A, mixed with Orange-Red 34 A. Flower throat (inside): RHS Greyed-Orange 176 A. Flower throat, vein: RHS Yellow-Green 152A. Flower tube (outside): RHS Yellow-Green 151 A. Flower tube, vein: RHS Yellow-Green 152 A.

*Fading*.—Petals Fading: to: RHS Greyed-Orange 174 A.

Calyx/sepals:

*Quantity per Flower*.—5.

*Shape*.—Linear.

*Length*.—About 1.5 cm.

*Width*.—About 0.2 cm.

*Apex*.—Rounded.

*Base*.—Cuneate.

*Margin*.—Entire.

*Texture*.—Velvety. Color: Upper Surface: RHS Green 137 B. Lower Surface: RHS Green 137 C.

Peduncle:

*Length*.—About 2 cm.

*Diameter*.—About 0.1 cm.

*Color*.—RHS Green 137 B.

*Orientation*.—45 degrees.

Fragrance: None.

REPRODUCTIVE ORGANS

Stamens:

*Number*.—5.

*Filament length*.—About 2.0 cm.

Anthers:

*Length*.—About 0.1 cm.

*Shape*.—Rounded.

*Color*.—RHS Yellow-White 158 A.

*Pollen*.—Color: RHS Yellow-White 158 A. Quantity: Abundant.

Pistil:

*Number*.—1.

*Length*.—About 2 cm.

*Style*.—Length: About 2 cm. Color: RHS Yellow-Green 149 D.

*Stigma*.—Shape: Rounded. Color: RHS Green 143 B. Ovary Color: RHS Green 143 A.

OTHER CHARACTERISTICS

Seeds and fruits: About 50 brown, rounded seeds of about 0.5 mm diameter, per one brown, conical capsule. Seeds minute, not well measured with an RHS chart.

Disease/pest resistance: Neither resistance nor susceptibility to normal diseases and pests of *Petunia* has been observed.

Temperature tolerance: Tolerates a range from approximately 5° to 40° C.

What is claimed is:

1. A new and distinct cultivar of *Petunia* plant named 'DCAS303' as herein illustrated and described.

* * * * *